(12) United States Patent
Putzig

(10) Patent No.: US 7,732,383 B2
(45) Date of Patent: Jun. 8, 2010

(54) PROCESS FOR STABILIZED ZIRCONIUM TRIETHANOLAMINE COMPLEX AND USES IN OIL FIELD APPLICATIONS

(75) Inventor: Donald Edward Putzig, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 505 days.

(21) Appl. No.: 11/643,120

(22) Filed: Dec. 21, 2006

(65) Prior Publication Data

US 2008/0149333 A1    Jun. 26, 2008

(51) Int. Cl.
    C23F 11/18    (2006.01)
    E21B 33/00    (2006.01)
    E21B 43/26    (2006.01)
    C09K 8/68     (2006.01)
    C23F 11/14    (2006.01)

(52) U.S. Cl. .................... 507/271; 166/285; 166/308.3; 507/211; 507/244

(58) Field of Classification Search .................. 507/244, 507/211, 271; 166/285, 308.3
See application file for complete search history.

(56) References Cited

U.S. PATENT DOCUMENTS

| | | |
|---|---|---|
| 4,460,751 A | 7/1984 | Hanlon et al. |
| 4,477,360 A | 10/1984 | Almond |
| 4,578,488 A | 3/1986 | Rummo et al. |
| 4,657,081 A | 4/1987 | Hodge |
| 4,683,068 A | 7/1987 | Kucera |
| 4,686,052 A | 8/1987 | Baranet et al. |
| 4,702,848 A | 10/1987 | Payne |
| 4,749,041 A | 6/1988 | Hodge |
| 4,797,216 A | 1/1989 | Hodge |
| 5,165,479 A | 11/1992 | Harris et al. |
| 5,271,466 A | 12/1993 | Harms |
| 5,273,580 A | 12/1993 | Totten et al. |
| 5,466,846 A | 11/1995 | Sharif |
| 5,558,161 A | 9/1996 | Vitthal et al. |
| 5,798,320 A | 8/1998 | Dawson et al. |
| 5,849,674 A | 12/1998 | Fox et al. |
| 5,950,731 A | 9/1999 | Shuchart et al. |
| 6,186,235 B1 | 2/2001 | Tjon-Joe-Pin et al. |
| 6,214,773 B1 | 4/2001 | Harris et al. |
| 6,454,008 B1 | 9/2002 | Chatterji et al. |
| 6,488,091 B1 | 12/2002 | Weaver et al. |
| 6,613,720 B1 | 9/2003 | Feraud et al. |
| 6,734,146 B2 | 5/2004 | Chatterji et al. |
| 6,793,018 B2 | 9/2004 | Dawson et al. |
| 6,810,959 B1 | 11/2004 | Qu et al. |
| 6,814,145 B2 | 11/2004 | Maberry et al. |
| 6,818,598 B2 | 11/2004 | Maberry et al. |
| 6,918,445 B2 | 7/2005 | Todd et al. |
| 6,971,448 B2 | 12/2005 | Slabaugh et al. |
| 6,983,801 B2 | 1/2006 | Dawson et al. |
| 7,001,872 B2 | 2/2006 | Pyecroft et al. |
| 7,036,590 B2 | 5/2006 | Harris |
| 2003/0092584 A1 | 5/2003 | Crews |
| 2003/0114539 A1 | 6/2003 | Weaver et al. |
| 2004/0211568 A1 | 10/2004 | Funkhouser et al. |
| 2004/0238169 A1 | 12/2004 | Todd et al. |
| 2005/0137094 A1 | 6/2005 | Weaver et al. |
| 2005/0178553 A1 | 8/2005 | Harris |
| 2005/0211435 A1 | 9/2005 | Monroe et al. |
| 2005/0269099 A1 | 12/2005 | Stegent et al. |
| 2005/0284637 A1 | 12/2005 | Stegent et al. |
| 2006/0009363 A1 | 1/2006 | Crews |
| 2006/0030493 A1 | 2/2006 | Segura |
| 2006/0032636 A1 | 2/2006 | Lord et al. |

FOREIGN PATENT DOCUMENTS

| | | |
|---|---|---|
| GB | 2 108 122 A | 5/1983 |
| WO | WO 2006/010912 A1 | 2/2006 |

OTHER PUBLICATIONS

Zhao et al., Zirconium Gel Water Shutoff Agent Used In Single Fluid Method; Shiyou Daxue Xuebao, Ziran Kexueban (1996), 20(1), 43-47; University of Petroleum, Dongying, 257062, Peop. Rep. China.

Primary Examiner—Timothy J. Kugel
Assistant Examiner—Aiqun Li
(74) Attorney, Agent, or Firm—Kathryn M. Sanchez

(57) ABSTRACT

A process for preparing a stable zirconium triethanolamine cross-linking agent comprises contacting a solution of a zirconium triethanolamine complex with water at a temperature of 50° C. to 90° C. at a mole ratio of triethanolamine:zirconium in the range of 3.5:5.5 and at a mole ratio of water:zirconium in the range of 20:1 to 1:1. The stable zirconium triethanolamine complex can be used in a cross-linking composition. Further disclosed are methods to use the composition in oil field applications for hydraulic fracturing and plugging of permeable zones and leaks in subterranean formations.

20 Claims, No Drawings

PROCESS FOR STABILIZED ZIRCONIUM TRIETHANOLAMINE COMPLEX AND USES IN OIL FIELD APPLICATIONS

FIELD OF THE INVENTION

The invention relates to the field of preparing zirconium cross-linking agents and their use in cross-linking compositions for oil well fracturing and permeable zone plugging applications. The cross-linking agent is a stabilized zirconium triethanolamine complex.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well via a conduit, such as tubing or casing, at a flow rate and a pressure which create, reopen and/or extend a fracture into the oil- or gas-containing formation. The proppant is carried into the fracture by the fluid composition and prevents closure of the formation after pressure is released. Leak-off of the fluid composition into the formation is limited by the fluid viscosity of the composition. Fluid viscosity also permits suspension of the proppant in the composition during the fracturing operation. Cross-linking agents, such as borates, titanates or zirconates are usually incorporated into the composition to control viscosity.

Normally, less than one third of available oil is extracted from a well after it has been fractured before production rates decrease to a point at which recovery becomes uneconomical. Enhanced recovery of oil from such subterranean formations frequently involves attempting to displace the remaining crude oil with a driving fluid, e.g., gas, water, brine, steam, polymer solution, foam, or micellar solution. Ideally, such techniques (commonly called flooding techniques) provide a bank of oil of substantial depth being driven into a producing well; however, in practice this is frequently not the case. Oil-bearing strata are usually heterogeneous, some parts of them being more permeable than others. As a consequence, channeling frequently occurs, so that the driving fluid flows preferentially through permeable zones depleted of oil (so-called "thief zones") rather than through those parts of the strata which contain sufficient oil to make oil-recovery operations profitable.

Difficulties in oil recovery due to high permeability of zones may be corrected by injecting an aqueous solution of an organic polymer and a cross-linking agent into certain subterranean formations under conditions where the polymer will be cross-linked to produce a gel, thus reducing the permeability of such subterranean formations to driving fluid (gas, water, etc.). Polysaccharide- or partially hydrolyzed polyacrylamide-based fluids cross-linked with certain aluminum, titanium, zirconium and boron-based compounds are also used in these enhanced oil recovery applications.

Cross-linked fluids or gels, whether for fracturing a subterranean formation or for reducing permeability of a subterranean formation, are now being used in wells under a variety of temperature and pH conditions, where rates of cross-linking with known cross-linking compositions may be unacceptable.

U.S. Pat. No. 4,578,488 discloses adding water to a cooled solution of a zirconium complex having a mole ratio of triethanolamine:zirconium of 2:1 to 1:1, preferably, 2:1, with the amount of water being added at a mole ratio of water:zirconium of 3:1 to 0.5:1. In one example, in which water is added at 55° C., a hazy product resulted. The cross-linking rates of the triethanolamine zirconium complexes upon addition of water were very fast, generating highly viscous gels.

U.S. Pat. No. 4,683,068 discloses preparing a zirconium complex of triethanolamine under anhydrous conditions, at a mole ratio of triethanolamine:zirconium of 2-3:1. The zirconium complex is activated by addition of large volumes of water, in excess of 600-1000 moles water per mole of zirconium, to provide an active cross-linking agent which cross-links "almost instantaneous" when blended with a polysaccharide (hydroxypropylguar). This patent further discloses that the activated zirconium complexes have poor shelf life.

U.S. Pat. No. 4,686,052 discloses a process to stabilize zirconium cross-linking complexes in water by adding a large excess of an alkanolamine, such as triethanolamine. The mole ratio of triethanolamine:zirconium for stabilizing in the presence of water is at least 15:1, preferably at least 42:1, if cross-linked gel will be exposed to temperature>200° F. (93° C.). These complexes result in very slow cross-linking. The high loading of triethanolamine also renders these complexes undesirably expensive.

There is a need for compositions which cross-link at a desirable rate, especially within the range of 3-8 minutes, and that such cross-linking compositions are economical and stable in the presence of water. The present invention meets these needs.

SUMMARY OF THE INVENTION

This invention provides a process to prepare an economical, stable cross-linking agent which is a zirconium triethanolamine complex. The zirconium complex is surprisingly stable, that is, does not precipitate or decompose, in the presence of water. The zirconium triethanolamine complex is prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1 for a period of time sufficient to stabilize the zirconium triethanolamine complex in the presence of water. Typically, the solution of zirconium complex is contacted with water for a period of 2 to 12 hours. It should be appreciated by one skilled in the art that at a lower temperature the time required to stabilize the zirconium solution is higher, that is, 12 hours at 50° C. may be appropriate, and at a higher temperature the time required to stabilize the zirconium solution is lower, that is, 2 hours at 90° C., and that ranges for time at different temperatures are contemplated.

The cross-linking agent can be used in a cross-linking composition which comprises (a) an aqueous liquid, (b) a pH buffer, (c) a cross-linkable organic polymer, and (d) a solution of a zirconium cross-linking agent prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1.

The cross-linking composition of this invention is useful in oil field applications, for example, for hydraulically fracturing a subterranean formation using the composition. The composition of this invention is further useful for plugging permeable zones or leaks in a subterranean formation. The components of the cross-linking composition may be mixed prior to introducing them into the formation or the components can be introduced and permitted to react in the formation after a controllable period of time.

Surprisingly, in view of known cross-linking compositions comprising zirconium-triethanolamine complexes, the cross-linking composition of this invention has a desirable cross-linking rate of 3-8 minutes generating good viscosity, preferably in the range of 300 to 1000 centipoise (cp). If viscosity is too high, gel syneresis occurs wherein there is over-cross-linking of the polymer and water separates from the gel causing globules of the gel to form, which can no longer suspend the sand or other proppant.

The cross-linking composition of this invention is useful in oil field applications, for example, for hydraulically fracturing a subterranean formation. The solution of this invention is further useful for plugging permeable zones or leaks in subterranean formations.

This invention provides a method for hydraulically fracturing a subterranean formation which comprises using stable zirconium triethanolamine complex prepared in accordance with the process described herein. This method comprises introducing into a subterranean formation at a flow rate and pressure sufficient to create, reopen and/or extend a fracture in the formation, (a) an aqueous liquid; (b) a pH buffer; (c) a cross-linkable organic polymer; and (d) a solution of a zirconium cross-linking agent prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1.

This invention provides a method for plugging a permeable zone or leak in a subterranean formation which comprises introducing into said zone or said leak, (a) an aqueous liquid; (b) a pH buffer; (c) a cross-linkable organic polymer; and (d) a solution of a zirconium cross-linking agent prepared by a process comprising contacting a solution of a zirconium tri-ethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1.

The present invention provides methods for effective viscosity generation in oil field applications such as fluid fracturing and plugging permeable zones. Surprisingly, the cross-linking composition of this invention cross-links to achieve maximum viscosity in a desirable 3 to 8 minute range at moderate well temperatures, such as 121-177° C. (250-350° F.), whereas in general, triethanolamine zirconium complexes have rates of cross-linking that are too fast, or when combined with large volumes of water or at high mole ratios of triethanolamine:zirconium, the rates of cross-linking of triethanolamine zirconium complexes are too slow.

DETAILED DESCRIPTION OF THE INVENTION

This invention provides a process to prepare a solution of a zirconium cross-linking agent, a cross-linking composition comprising the solution thus prepared and methods for use of the composition, especially in oil well applications such as methods for hydraulic fracturing and plugging of permeable zones in which rate of cross-linking of a cross-linkable polymer is in the range of 3-8 minutes, achieving a viscosity of 300 to 1000 centipoise (cp), preferably 450 to 850 cp. The product of the process is a clear solution, stable to water, that is, free of haze or precipitation over time. More specifically, no precipitation occurs for at least one month, preferably at least three months, more preferably at least six months. The concentration of zirconium in the stable solution is generally less than 15% by weight, preferably in the range of 5-15% Zr by weight, more preferably in the range of 8-13% by weight.

The process of this invention comprises or consists of contacting a solution of a zirconium triethanolamine complex with water at a temperature of 50° C. to 90° C. for a period of time sufficient to stabilize the zirconium triethanolamine solution in the presence of water by forming a clear solution. To provide a stable, clear solution, the mole ratio of triethanolamine:zirconium is in the range of 3.5:1 to 5.5:1, preferably, 4:1 to 5:1, more preferred the mole ratio of triethanolamine:zirconium is 4:1. In addition, the mole ratio of water:zirconium is in the range of 20:1 to 1:1, preferably 15:1 to 5:1, more preferably 12:1 to 8:1. If too little triethanolamine is added, the solution will be unstable. If too much triethanolamine is added, the solution will cross-link too slow. If too little water is added, the solution will cross-link too fast. If too much water is added, the solution will be unstable.

Typically the starting solution of zirconium triethanolamine complex is contacted with water at the temperature of 50-90° C. for a period of 2 to 12 hours. It should be appreciated by those skilled in the art that at lower temperatures, longer times are needed to stabilize the solution of zirconium complex in the presence of water at lower temperatures and shorter times are needed to stabilize the solution of zirconium complex at higher temperatures.

The starting solution of zirconium complex is a solution of a zirconium triethanolamine complex in an organic solvent. Preferred solvents are $C_1$-$C_6$ alcohols, more preferred are $C_3$-$C_4$ alcohols. A preferred starting zirconium triethanolamine complex is a solution of zirconium tetratriethanolamine, such as Tyzor® TEAZ organic zirconate, available from E. I. du Pont de Nemours and Company, Wilmington, Del.

The present invention provides a cross-linking composition which comprises (a) an aqueous liquid; (b) a pH buffer; (c) a cross-linkable organic polymer; and (d) a stable solution of a zirconium cross-linking agent prepared by a process comprising or consisting of contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1.

The solution of zirconium cross-linking agent is the clear, stable solution prepared as described above.

The cross-linking composition comprises an effective amount of a pH buffer to control pH. The pH buffer may be acidic, neutral or basic. The pH buffer is generally capable of controlling the pH from about pH 3 to about pH 12. For example, in a composition for use at pH of about 4-5, an acetic acid-based buffer can be used. In a composition for use at a pH of 5-7, a fumaric acid-based buffer or a sodium diacetate-based buffer can be used. In a composition for use at a pH of 7-8.5, a sodium bicarbonate-based buffer can be used. In a composition for use at a pH of 9-12, a sodium carbonate or sodium hydroxide-based buffer can be used. Other suitable pH buffers can be used, as are known to those skilled in the art.

The composition further comprises a cross-linkable organic polymer. Suitable cross-linkable organic polymers are selected from the group consisting of solvatable polysaccharides, polyacrylamides and polymethacrylamides. Preferably the organic polymer is a solvatable polysaccharide and is selected from the group consisting of gums, gum derivatives and cellulose derivatives. Gums include guar gum and locust bean gum, as well as other galactomannan and glucomannan gums, such as those derived from sennas, Brazilwood, tera, honey locust, karaya gum and the like. Gum derivatives include hydroxyethylguar (HEG), hydroxypropylguar (HPG), carboxyethylhydroxyethylguar (CEHEG), carboxymethylhydroxypropylguar (CMHPG), carboxymethyl guar (CMG), and the like. Cellulose derivatives include those containing carboxyl groups, such as carboxymethylcellulose (CMC), carboxymethylhydroxyethylcellulose (CMHEC), and the like. The solvatable polysaccharides can be used individually or in combination; usually, however, a single material is used. Guar derivatives and cellulose derivatives are preferred, such as, HPG, CMC and CMHPG. HPG is generally more preferred based upon its commercial availability and desirable properties. However, CMC and CMHPG may be more preferred in cross-linking compositions when the pH of the composition is less than 6.0 or higher than 9.0, or when the permeability of the formation is such that one wishes to keep the residual solids at a low level to prevent damage to the formation.

The cross-linkable polymer is normally mixed with the aqueous liquid to form a base gel. The aqueous liquid is water or a mixed water/organic solvent or an aqueous solution. Organic solvents that may be used include alcohols, glycols, polyols, and hydrocarbons such as diesel. As an example, the polymer may be mixed with an aqueous liquid selected from the group consisting of water, a water/alcohol mixture (e.g., where the alcohol is methanol or ethanol), and an aqueous solution comprising a clay stabilizer. Clay stabilizers include, for example, hydrochloric acid and chloride salts, such as, tetramethylammonium chloride (TMAC) or potassium chloride. Aqueous solutions comprising clay stabilizers may comprise, for example, 0.05 to 0.5 weight % of the stabilizer, based on the total weight of the cross-linking composition.

The composition may comprise optional components, including those which are common additives for oil field applications. Thus, the composition may further comprise one or more of proppants, friction reducers, bactericides, hydrocarbons, chemical breakers, stabilizers, surfactants, formation control agents, and the like. Proppants include sand, bauxite, glass beads, nylon pellets, aluminum pellets and similar materials. Friction reducers include polyacrylamides. Hydrocarbons include diesel oil. Chemical breakers break the cross-linked polymer (gel) in a controlled manner and include enzymes, alkali metal persulfate, and ammonium persulfate. Stabilizers include methanol, alkali metal thiosulfate, and ammonium thiosulfate. Stabilizers may also include clay stabilizers such as hydrochloric acid and chloride salts, for example, tetramethylammonium chloride (TMAC) or potassium chloride.

These optional components are added in an effective amount sufficient to achieve the desired cross-linking performance based on the individual components, desired delay in cross-linking time, temperature and other conditions present in the formation being fractured or permeable zone being plugged.

The cross-linking composition is produced by mixing the stable solution of zirconium complex with the other components, in any order. For example, in one particular application in an oil field, the solution of zirconium complex with optional components are introduced into a formation, while the cross-linkable organic polymer is introduced into the formation as a separate stream. Alternatively, all components may be premixed and introduced into a subterranean formation as a single stream. Advantageously, the components may be mixed in different combinations, and more advantageously, the components may be mixed just prior to use to enable easy variation and adjustment of the cross-linking rate.

This invention provides a method for hydraulically fracturing a subterranean formation, which comprises introducing into the formation at a flow rate and pressure sufficient to create, reopen, and/or extend one or more fractures in the formation, a cross-linking composition comprising an aqueous liquid; a pH buffer; a cross-linkable organic polymer; and a stable solution of a zirconium cross-linking agent prepared by a process comprising or consisting of contacting a solution of a zirconium triethanolamine complex with water at a temperature of 50° C. to 90° C. at a mole ratio of triethanolamine: zirconium in the range of 3.5:1 to 5.5:1 and at a mole ratio of water:zirconium in the range of 20:1 to 1:1; and other optional components.

In one embodiment of the method for hydraulically fracturing a subterranean formation, the stable solution of zirconium complex and the cross-linkable polymer are contacted prior to their introduction into the formation, such that the zirconium cross-linking agent and polymer react to form a cross-linked gel, wherein the gel is introduced into the formation. In this method, a cross-linking composition is prepared by mixing a solution comprising the stable solution of zirconium complex with a base gel. A base gel is prepared by mixing a cross-linkable organic polymer with an aqueous liquid. This method comprises contacting the solution of zirconium complex with the base gel; permitting the zirconium cross-linking agent and the base gel to react, to form a cross-linked gel; and introducing the cross-linked gel into the formation at a flow rate and pressure sufficient to create, reopen, and/or extend a fracture in the formation. The stable solution of zirconium complex, the base gel, or both further comprise a pH buffer.

Alternatively, the subterranean formation may be penetrated by a wellbore, such that contacting the stable solution of zirconium complex with the base gel occurs in the wellbore and the cross-linked gel is introduced into the formation from the wellbore. This method of hydraulically fracturing a subterranean formation penetrated by a wellbore comprises (a) preparing a base gel by mixing a cross-linkable organic polymer with an aqueous liquid; (c) introducing the base gel into the wellbore; (d) simultaneously with or sequentially after, introducing the base gel into the wellbore, introducing a stable solution of a zirconium cross-linking agent prepared by a process comprising or consisting of contacting a solution of a zirconium triethanolamine complex with water at a temperature of 50° C. to 90° C. at a mole ratio of triethanolamine: zirconium in the range of 3.5:1 to 5.5:1 and at a mole ratio of water:zirconium in the range of 20:1 to 1:1, into the wellbore; (e) permitting the base gel and the zirconium cross-linking agent to react to form a cross-linked aqueous gel; and (e) introducing the cross-linked gel into the formation from the wellbore at a flow rate and pressure sufficient to create, reopen, and/or extend a fracture in the formation. A pH buffer is independently admixed with the base gel, the stable solution of zirconium complex or both prior to introducing the base gel and the stable solution of zirconium complex into the wellbore.

Upon creation of a fracture or fractures, the method may further comprise introducing a cross-linking composition comprising the stable solution of zirconium complex, a cross-linkable organic polymer and proppant into the fracture or fractures. This second introduction of the stable solution of zirconium complex is preferably performed in the event the cross-linking composition used to create the fracture or fractures did not comprise proppant.

Another use for the stable solution of zirconium complex prepared according to the process of the present invention relates to a method for selectively plugging permeable zones and leaks in subterranean formations which comprises introducing into the permeable zone or the site of the subterranean leak, a cross-linking composition comprising (a) an aqueous liquid; (b) a pH buffer; (c) a cross-linkable organic polymer; and (d) a stable solution of a zirconium cross-linking agent prepared by a process comprising or consisting of contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1, into the permeable zone or the site of the subterranean leak. The pH buffer may be admixed with the stable solution of zirconium complex prior to introducing the cross-linking composition into the permeable zone or site of the leak.

In a first embodiment of the method for plugging a permeable zone or a leak in a subterranean formation, the aqueous liquid, pH buffer, cross-linkable organic polymer and the stable solution of zirconium complex are contacted prior to their introduction into the subterranean formation, such that the polymer and the zirconium cross-linking agent react to form a cross-linked aqueous gel, which gel is then introduced into the formation.

In an alternative embodiment of the method for plugging a permeable zone or a leak in a subterranean formation, the stable solution of zirconium complex and the cross-linkable organic polymer are introduced separately, either simultaneously or sequentially, into the permeable zone or the site of the subterranean leak such that cross-linking occurs within the subterranean formation. This method comprises (a) preparing a base gel by mixing a cross-linkable organic polymer with an aqueous liquid; (b) introducing the base gel into the into the permeable zone or the site of the subterranean leak; (d) simultaneously with or sequentially after, introducing the base gel into the into the permeable zone or the site of the subterranean leak, introducing the stable zirconium solution prepared as described herein, into the into the permeable zone or the site of the subterranean leak; (e) permitting the base gel and the cross-linking agent to react to form a cross-linked aqueous gel to plug the zone and/or leak. The stable solution of zirconium complex, the base gel, or both further comprise a pH buffer.

The relative amounts of cross-linkable organic polymer and the zirconium cross-linking agent may vary. One uses small but effective amounts which for both will vary with the conditions, e.g., the type of subterranean formation, the depth at which the method (e.g., fluid fracturing, permeable zone plugging or leak plugging) is to be performed, temperature, pH, etc. Generally one uses as small an amount of each component as will provide the viscosity level necessary to effect the desired result, i.e., fracturing of the subterranean formation, or plugging permeable zones or leaks to the extent necessary to promote adequate recovery of oil or gas from the formation.

For example, satisfactory gels can generally be made for fluid fracturing by using the cross-linkable organic polymer in amounts up to about 1.2 weight % and the cross-linking composition in amounts up to about 0.50 weight % of the zirconium cross-linking agent, with percentages being based on the total weight. Preferably, from about 0.25 to about 0.75 weight % of the cross-linkable organic polymer is used and from about 0.05 to about 0.25 weight % of the zirconium cross-linking agent is used.

In a method for plugging permeable zones or leaks, generally about 0.25 to 1.2 weight % of a cross-linkable organic polymer is used, preferably 0.40 to 0.75 weight %, based on the total weight. Generally about 0.01 to 0.50 weight % of the zirconium cross-linking agent is used, preferably 0.05 to 0.25 weight %, based on the total weight.

The amount of zirconium used to cross-link the organic polymer is that which provides a zirconium ion concentration in a range from about 0.0005 weight % to about 0.1 weight %, based on the total weight. The preferred concentration of zirconium ion is in the range of from about 0.001-0.05 weight %, based on the total weight.

Typically the stable solution of zirconium complex prepared according to the process of this invention can be used at a pH of from about 3 to 11. For low temperature applications (150-250° F., 66-121° C.), carbon dioxide-based energized fluids may be used. In this case, a pH for the cross-linking composition of about 3 to about 6 is preferred. For moderate or high temperature applications (250-400° F., 121-204° C.), a pH of about 9 to about 11 is preferred. Advantageously, the stable solution of zirconium complex of this invention is used at a temperature of 275-325° F. (135-163° C.).

EXAMPLES

Methods

Preparation of Base Gel

A Waring blender jar was filled with 1 liter of distilled water. To this was added 2 g of a 50% aqueous solution of tetramethylammonium chloride clay stabilizer. Agitation was started and 3.6 g of carboxymethylhydroxypropylguar (CM-HPG) was sprinkled into the vortex of the agitating solution. The pH of the resultant slurry was adjusted to 6 with sodium diacetate and agitation continued for 30 minutes. The pH was then adjusted to 10.3 with 10% sodium hydroxide solution. Agitation was stopped and the gel was allowed to stand for 30 minutes or more before use.

Viscosity Measurement of Zirconate Cross-Linked Base Gel

To 250 ml of a vigorously agitated sample of base gel in a Waring blender jar, was added 0.00032 moles of zirconium (0.2-1.0 ml dependent on percent zirconium of cross-linker solution—hereinafter referred to as the Standard Loading Density). Agitation was continued for about 15-180 seconds. A 25 ml sample of the cross-linker containing gel was placed in the cup of the FANN 50 Viscometer with an R-1, B-3 configuration and viscosity was measured at 275° F. (135° C.) and 122 rpm at 100 reciprocal seconds of shear.

The Table shows the performance of a 30 lb/1000 gallon (3600 g/1000 liters) CMHPG gel cross-linked with the known zirconate (Control) and those of the invention. For the solutions of Examples Control Triethanolamine (135.2 g) was added to 100 g of tetra-n-propylzirconate solution (Tyzor® NPZ organic zirconate, available from E. I. du Pont de Nemours and Company, Wilmington, Del.). The reaction mixture was heated to 60° C. and held at this temperature for 4 hours. Upon completion of the reaction the resultant solution was concentrated on a rotary evaporator under reduced pressure to yield 155 g of a viscous yellow oil, which contained 13.2% Zr.

Comparative Example A

A 500 ml flask equipped with an agitator, condenser, nitrogen bubbler and dropping funnel was charged with 220.3 g (0.5 moles) of tetra-n-propyl zirconate. Agitation was started and 74.5 g (0.5 moles) of triethanolamine were added. The mixture was heated to 60° C. and held at this temperature for 2 hours. During the heating period, a white solid separated from the reaction mass. Upon dilution with 9 g (0.5 moles) of water, the solids dissolved. The resultant solution was heated an additional 4 hours at 80° C. to give a 303 g of a pale yellow liquid containing 15% Zr. On standing for several days solids began to precipitate from solution. The combined solution/precipitate of a 1:1 mole ratio of triethanolamine:zirconium could not be used as a cross-linker.

Example 1

A 250-ml flask was charged with 180 g of zirconium tetra-triethanolamine (Tyzor® TEAZ organic zirconate, available from E. I. du Pont de Nemours and Company, Wilmington, Del.). Agitation was started and 20 g of water was added slowly. The mixture was heated to 80° C. and held at this temperature for 4 hours to give 200 g of a pale yellow solution containing 11.9% Zr. The product was stable for at least six months.

Example 2

A 250-ml flask was charged with 167 g of zirconium tetra-triethanolamine (Tyzor® TEAZ organic zirconate). Agitation was started and 33 g of water was added slowly. The mixture was heated to 80° C. and held at this temperature for 4 hours to give 200 g of a pale yellow solution containing 11.0% Zr. The product was stable for at least six months.

Example 3

A 250-ml flask was charged with 150 g of zirconium tetra-triethanolamine (Tyzor TEAZ organic zirconate). Agitation was started and 50 g of water was added slowly. The mixture was heated to 80° C. and held at this temperature for 4 hours to give 200 g of a pale yellow solution containing 9.9% Zr. The product was stable for at least six months.

TABLE

| Example | % Zr | Loading (ml) | Zirconium (moles) | Triethanol amine (moles) | Water (moles) | Time to maximum viscosity (min) | Maximum viscosity (cp) | Viscosity at 30 min (cp) | Viscosity at 60 min (cp) | Viscosity at 90 min (cp) |
|---|---|---|---|---|---|---|---|---|---|---|
| Control | 13.2 | 0.18 | 1 | 4 | 0 | 1.5 | 1125 | 580 | 680 | 660 |
| 1 | 11.9 | 0.25 | 1 | 4 | 4.27 | 6.5 | 690 | 530 | 530 | 530 |
| 2 | 11.0 | 0.27 | 1 | 4 | 8.92 | 6 | 900 | 650 | 665 | 660 |
| 3 | 9.9 | 0.30 | 1 | 4 | 12.74 | 4 | 1225 | | | 790 |
| 3 | 9.9 | 0.30 | 1 | 4 | 12.74 | 7.5 | 540 | 465 | 450 | 430 |

As can be seen from the Table, the zirconium-triethanolamine cross-linking composition in the Control generates excellent viscosity; however its rate of cross-linking, as measured by time to reach maximum viscosity, is much too fast at 1.5 minutes. In the field, at this rate of cross-linking, it would be expected that shear degradation and loss of viscosity of the cross-linked gel would occur, prior to reaching the zone to be fractured or plugged in the formation.

As can be seen from the Table, the rate of cross-linking for the solutions of zirconium complex prepared according to the process of this invention are within the desirable range of 3-8 minutes. At these cross-linking rates, the cross-linking compositions can be used in the field for fracturing or plugging, even for hotter, deeper formations. Initial viscosity development with these cross-linkers is somewhat lower, but viscosity retention after 90 minutes is still excellent, which is also favorable for use in hot deep wells.

What is claimed is:

1. A process to prepare a zirconium cross-linking agent comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1 for a period of time sufficient to stabilize the zirconium triethanolamine complex in the presence of water having a cross-linking rate when combined with a cross-linkable polymer in the range of 3-8 minutes, achieving a viscosity of 300-1000 centipoise.

2. The process of claim 1 wherein the mole ratio of triethanolamine:zirconium is in the range of 4:1 to 5:1.

3. The process of claim 2 wherein the mole ratio of triethanolamine:zirconium is 4:1.

4. The process of claim 1 wherein the mole ratio of water:zirconium in the range of 15:1 to 5:1.

5. The process of claim 1 wherein the mole ratio of water:zirconium in the range of 12:1 to 8:1.

6. A cross-linking composition comprising (a) an aqueous liquid; (b) a pH buffer; (c) a cross-linkable organic polymer; and (d) a solution of a zirconium cross-linking agent prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1 wherein the cross-linking composition has a crosslinking rate in the range of 3-8 minutes, achieving a viscosity of 300-1000 centipoise.

7. The cross-linking composition of claim 6 wherein the cross-linkable organic polymer is selected from the group consisting of solvatable polysaccharides, polyacrylamides and polymethacrylamides.

8. The cross-linking composition of claim 7 wherein the cross-linkable organic polymer is a solvatable polysaccharide.

9. The cross-linking composition of claim 8 wherein the cross-linkable organic polymer is selected from the group consisting of gums, gum derivatives and cellulose derivatives.

10. The cross-linking composition of claim 9 wherein the cross-linkable organic polymer is hydroxypropylguar, carboxymethylhydroxypropylguar, or carboxymethylcellulose.

11. The cross-linking composition of claim 6 wherein the cross-linkable polymer is mixed with an aqueous liquid.

12. The cross-linking composition of claim 11 wherein the aqueous liquid is an aqueous solution comprising a clay stabilizer.

13. The cross-linking composition of claim 12 wherein the clay stabilizer is hydrochloric acid, tetramethylammonium chloride or potassium chloride.

14. A method for hydraulically fracturing a subterranean formation comprising introducing into a subterranean formation at a flow rate and pressure sufficient to create, reopen and/or extend a fracture in the formation, (a) an aqueous liquid; (b) a pH buffer; (c) a cross-linkable organic polymer; and (d) a solution of a zirconium cross-linking agent prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1 wherein the cross-linking composition has a crosslinking rate in the range of 3-8 minutes, achieving a viscosity of 300-1000 centipoise.

15. The method of claim 14 wherein the aqueous liquid, pH buffer, cross-linkable organic polymer; and solution of the zirconium cross-linking agent are contacted prior to their introduction into the subterranean formation.

16. The method of claim 14 wherein the subterranean formation is penetrated by a wellbore and contacting of the zirconium solution of (d) with the aqueous liquid (a) and the cross-linkable organic polymer (c) occurs in the wellbore.

17. The method of claim 14 further comprising introducing (e) proppant into the subterranean formation.

18. A method for plugging a permeable zone or leak in a subterranean formation comprising introducing into said zone or said leak, (a) an aqueous liquid; (b) a pH buffer; (c) a cross-linkable organic polymer; and (d) a solution of a zirconium cross-linking agent prepared by a process comprising contacting a solution of a zirconium triethanolamine complex with water at a temperature of 50° C. to 90° C. at a mole ratio of triethanolamine:zirconium in the range of 3.5:1 to 5.5:1 and at a mole ratio of water:zirconium in the range of 20:1 to 1:1 wherein the cross-linking composition has a crosslinking rate in the range of 3-8 minutes, achieving a viscosity of 300-1000 centipoise.

19. The method of claim 18 wherein the aqueous liquid, pH buffer, cross-linkable organic polymer; and solution of the zirconium cross-linking agent are contacted prior to their introduction into the subterranean formation.

20. The method of claim 18 wherein the subterranean formation is penetrated by a wellbore and contacting of the zirconium solution of (d) with the aqueous liquid (a) and the cross-linkable organic polymer (c) occurs in the wellbore.

* * * * *